United States Patent [19]

Murphy

[11] Patent Number: 5,610,837
[45] Date of Patent: Mar. 11, 1997

[54] SYSTEM AND METHOD FOR NONDESTRUCTIVE VIBRATIONAL TESTING

[75] Inventor: Joseph F. Murphy, Madison, Wis.

[73] Assignee: Sonoco Products Company, Hartsville, S.C.

[21] Appl. No.: 230,947

[22] Filed: Apr. 21, 1994

[51] Int. Cl.$^6$ .................................................... G06G 7/19
[52] U.S. Cl. .............................................. 364/508; 364/576
[58] Field of Search ..................................... 364/508, 507, 364/576, 579, 580; 73/593, 658, 660, 661, 602

[56] References Cited

U.S. PATENT DOCUMENTS

| | | | |
|---|---|---|---|
| 3,513,690 | 5/1970 | Pellerin et al. | 73/67 |
| 4,520,674 | 6/1985 | Canada et al. | 73/660 |
| 4,885,707 | 12/1989 | Nichol et al. | 364/508 |
| 4,979,125 | 12/1990 | Kwun et al. | 364/508 |
| 5,179,860 | 1/1993 | Tsuboi | 364/508 |
| 5,289,387 | 2/1994 | Hige et al. | 364/508 |
| 5,388,056 | 2/1995 | Horiuchi et al. | 364/508 |

OTHER PUBLICATIONS

Ross et al., "Transverse Vibration nondestruction testing using on personal computer", Aug. 1991.

*Primary Examiner*—James P. Trammell
*Attorney, Agent, or Firm*—Dennison, Meserole, Pollack & Scheiner

[57] ABSTRACT

The present invention is a system and method for nondestructive vibrational testing of a specimen, such as a paper core tube. The system analyzes transverse vibrations of the simply supported specimen. The system measures the weight change at one end of the specimen and determines the frequency of vibration and the rate of energy loss. The testing is such that the specimen can be used after testing.

20 Claims, 4 Drawing Sheets

SYSTEM AND METHOD FOR NONDESTRUCTIVE VIBRATIONAL TESTING

BACKGROUND OF THE INVENTION

1. Field of Invention

The invention relates to a method and apparatus for determining the frequency of vibration and rate of energy loss for a stiff structure.

2. Discussion of Prior Art

Heretofore, considerable efforts have been devoted to developing nondestructive testing for evaluating the quality of stiff structures, such as lumber, products of paper and products of steel. The most widely used test is based on a flatwise bending test. Stiffness is measured by using a load-deflection relationship of a simple supported beam loaded at its mid-span. The modulus of elasticity of the structure or specimen is determined by measuring the bending deflection resulting from a known load.

A detailed theory of the mathematical principles of vibration testing are discussed in "A Vibrational Approach to . . . Nondestructive Testing of Structural Lumber", by Roy F. Pellerin, Forest Products Journal, Vol. XV3, March 1965, p. 93–101.

Additionally, U.S. Pat. No. 3,513,690 to Pellerin et al. discloses a method and apparatus for nondestructive testing of wood beams. The apparatus measures vibrations at the center of the span for a given wood specimen. Pellerin et al. utilizes a well known relationship between modulus of elasticity and the frequency of oscillation of a simply supported beam (Timoshenko, Young and Weaver, 1974). Drawbacks to this apparatus are that there is no adjustment or consideration for the difference between the span of the beam and the length of the beam. Also, the log decrement is determined using amplitude ratio of only two cycles and there are no computer or data logging parts. Additionally, Pellerin et al. does not measure the weight of the beam, only the vibration and vibration decay.

Recently, with the advancement of the personal computer, it has been possible to develop systems to perform fast fourier transform calculations to determine frequency of vibration. These FFT systems have greatly increased the capabilities of nondestructive testing of structural beams beyond the scope of the Pellerin et al. patent.

In early 1990, a nondestructive testing device for measuring the dynamic modulus of elasticity was developed. This data acquisition attachment, called DynaMOE™ requires a personal computer with an 80×87 math co-processor and an expansion slot. The device calculates the modulus of elasticity and a parameter relating to internal friction for softwood and hardwood timbers to determine strength properties. A weakness of this device is that it requires a computer with a math co-processor and an expansion slot. Additionally, the sampled data are restricted to 512 points and the user must trigger the data acquisition of the system.

The U.S. Department of Agriculture, Forest Service, Forest Products Laboratory, published in August 1991, a paper titled, "Transverse Vibration Nondestructive Testing Using a Personal Computer", FPL-RP-502. The system utilized a lap-top personal computer to collect data from lumber specimens subjected to transverse vibrations. The data were used to compute dynamic modulus of elasticity using a flatwise bending test. Problems with this system relate to the analysis. The system is restricted to 512 Points, and the user must trigger the acquisition system. The system is only capable of displaying numerical results and specimens tested must have rectangular cross sections.

The nondestructive testing systems exemplified in the literature referred to hereinabove demonstrate many improvements made over the years in computerizing and improving the technology of transverse vibration testing systems. There still exists, however, in this industry, a need for a self-contained data acquisition which particularly improves the capabilities, efficiencies and economy of transverse vibration testing devices as well as simplifies installation and operation.

SUMMARY OF INVENTION

The present invention is a nondestructive vibration testing system. The system is a separate self-contained unit which readily attaches to any IBM compatible personal computer. The present invention measures the weight change and determines the frequency of vibration as well as the rate of energy loss. The system is capable of testing a wide range of specimens, such as paper core tubes, wood beams and steel elements.

Accordingly, it is an object of the invention to be a self-contained system separate and distinct from the user's personal computer.

It is an object of the invention to have an analog to digital capability in the separate and distinct system.

Another object of the invention is to have various sized load cells wherein each load cell has an electronically adjustable scale.

Another object of the invention is to be capable of utilizing a math co-processor.

A further object of the invention is to calculate, using fast fourier transform operations and nonlinear least squares procedures, vibration frequency to a resolution of 0.001 Hz.

An advantage of the invention is that the user is capable of inputting the weight, length, span, outer diameter and wall thickness of the specimen to be tested.

It is an advantage of the invention that the system provides the user with 1536 total data samples and the user selects 512 data samples to be analyzed.

A further advantage of the invention is that the data acquisition is triggered by the vibrations.

An additional advantage of the invention is that the system calculates frequency and log decrement of the specimen.

Another advantage of the invention is that the system can be used to test paper core tubes as specimens wherein the tubes can be used after testing.

A further advantage of the invention is that the system can determine the core stiffness of the specimen.

An additional advantage of the invention is that the system can determine the core modulus of the specimen.

It is an object of the invention to display numerical results, graphic data and theoretical curves of the tested specimen.

It is another object of the invention to display a numeric measure of fit calculated as a normalized standard error of estimate for the tested specimen.

An additional object of the invention is to store the results of the testing and save the original data as well as all inputted data.

Further objects and advantages of the invention will become apparent from a consideration of the drawings and ensuing description.

DESCRIPTION OF THE INVENTION

Figure 1:
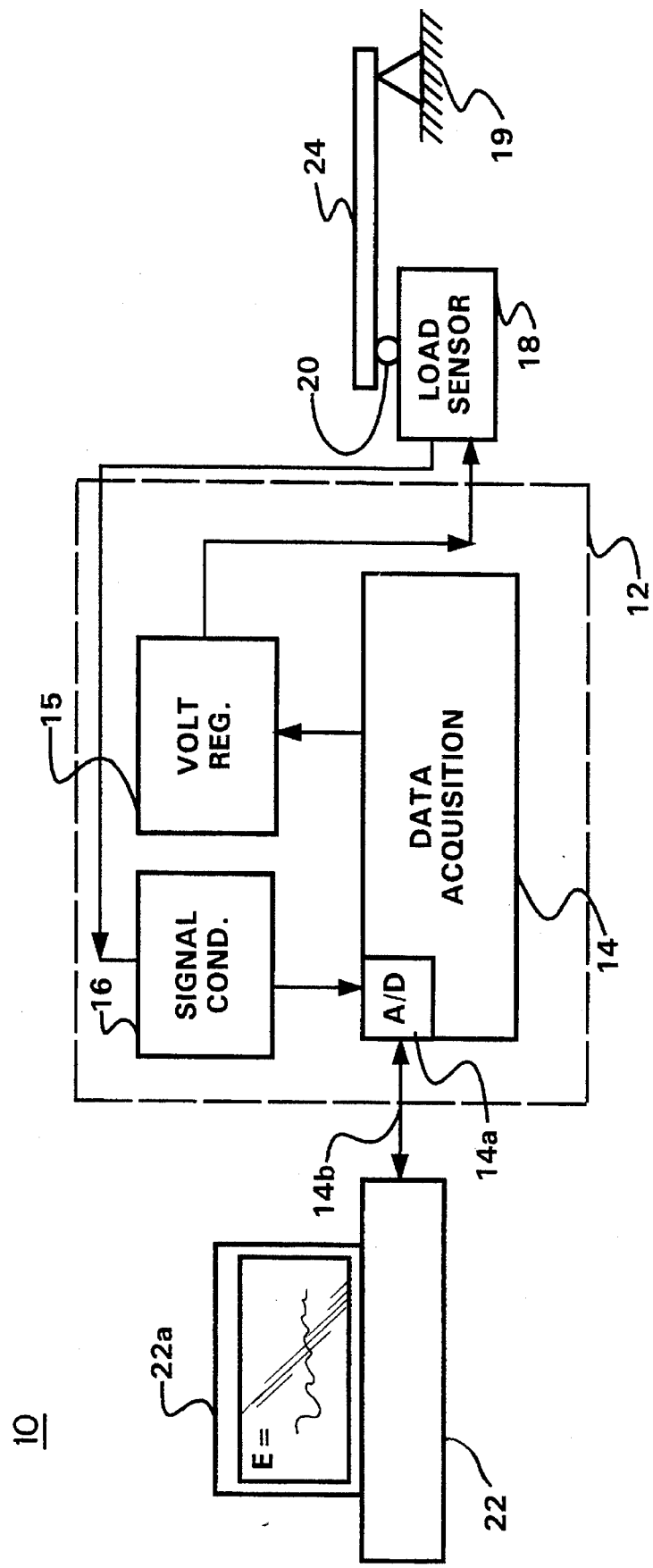
FIG. 1 is a circuit block diagram of the present invention.

FIG. 1 illustrates the nondestructive vibrational testing system generally indicated by reference numeral 10. The system includes a number of readily detachable components. There is a computer hardware system 12 which includes a data acquisition section 14. The data acquisition section 14 has an analog-to-digital (A/D) section or card 14a for converting data. The system 12 also includes a voltage regulating circuit 15 and a signal conditioning circuit 16.

Computer hardware system 12 consists of a stand-alone computer with serial interface 14b connected to an IBM-compatible computer 22, an A/D card 14a a card with a voltage regulation circuit 15 connected to a load sensor 18, and a circuit 16 to condition the signal from the load sensor 18 for provision to the A/D card 14a. Alpha Products of Fairfield, Conn. is a manufacturer of such cards. The present embodiment utilizes the A-Bus Motherboard MB-120, Stand-alone Controller SP-127, Fast 12-bit A/D FA-154, and Prototype Card PR-152. The Prototype Card has a voltage regulation circuit and signal conditioning circuit such as Burr-Brown Instrument Amplifier INA110.

Connected to the computer hardware system 12 is a load sensor device 18 which is associated with a support 19. The support 19 has a knife type edge and is built so as not to respond to vibrations. In other words, support 19 is a fixed stationary support. The load sensor device 18 also is associated with a load cell 20 and the sensor 18 is a common off-the-shelf type device. A manufacturer of load cells is Interface Inc. in Scottsdale, Ariz. In the present embodiment, model number SPI-50 is utilized.

As shown in the FIG. 1, computer hardware system 12 is connected to an IBM compatible computer 22 which includes a monitor 22a for displaying generated data and a keyboard (not shown) for inputting data. The method is illustrated in flowchart form in FIGS. 2A and 2B and is entered by floppy diskette into computer 22. The method follows the mathematical theory of operation set forth in Pellerin, R. F., "A Vibrational Approach . . . Nondestructive Testing of Structural Lumber," Forest Products Journal, Vol. XV3, March, 1965), p. 93–101. The following analysis summarizes the theory.

Mathematically, the relationship between dynamic modulus of elasticity, $E_d$, and frequency, f, of a transversely vibrating prismatic member, simply supported at its ends, is:

$$E_d = \frac{f^2 W L^3}{2.46 g I} \quad [1]$$

where Equation [1] is valid for a prismatic member of uniform cross section, i.e., rectangular beams or panels, or I-joists, and W=weight of member, L=length of the member, I=moment of inertia about axis perpendicular to vibrating direction, g=acceleration of gravity, and 2.46=a constant for simple end supports.

Because there has to be some overhang to support the prismatic member, L in Equation [1] is replaced by the span, S, between supports and W is multiplied by S/L to give the weight of the member between supports. Accordingly, the relationship becomes:

$$E_d = \frac{f^2 W S^4}{2.46 g I L} \quad [2]$$

Equation [2] can be simplified further if the member has a rectangular cross section, i.e., B=width and H=height. Equation [2] then becomes:

$$E_d = \frac{f^2 p S^4}{.205 g H^2} \quad [3]$$

where p is weight per unit volume and there is no width effect, B, in Equation [3].

The procedure starts when the user or tester transversely vibrates a paper core tube 24 positioned on the support 19 at the distal end and the load sensor device 18 at the proximal end. It should be noted at this point that neither the support 19 nor the load cell 20 are positioned at the immediate ends of the tube 24. Instead, the positioning of the tube 24 on the support 19 and cell 20 is such that there is some overhang and, as previously stated, the span compensates for this overhang.

Accordingly, the tube 24 is laid on the knife-edge support 19 at one end, and on the load cell 20 at the other. By pressing the tube 24 down at mid-span, and releasing it, the tube 24 vibrates vertically. The load cell 20 senses the changing reaction force and the computer hardware system 12 acquires the electronic signal from load sensor 18.

The nondestructive vibrational testing system 10 analyzes the decaying sine wave and determines the rate of energy loss according to $$w = e^{-(d/t)} \sin[2\pi f t] \quad [4]$$

The log decrement, d, has been found to correlate inversely with solid wood strength. A zero value of "d" would indicate no amplitude change of the sine wave (high strength). A large "d" value would mean high internal friction (low strength).

The system 10 records the signals and analyses the decaying sine wave. The average recorded force is the average reaction force on the load cell 20, and hence is half the weight of the tube 24. The frequency of the decaying sine wave is "f". Knowing the member geometry, member weight and frequency, the dynamic modulus of elasticity, E, can be calculated, (see Equations [1], [2] and [3]). The measured E is used to "grade" the board, panel or tube 24 or check for quality assurance.

Figure 2A:
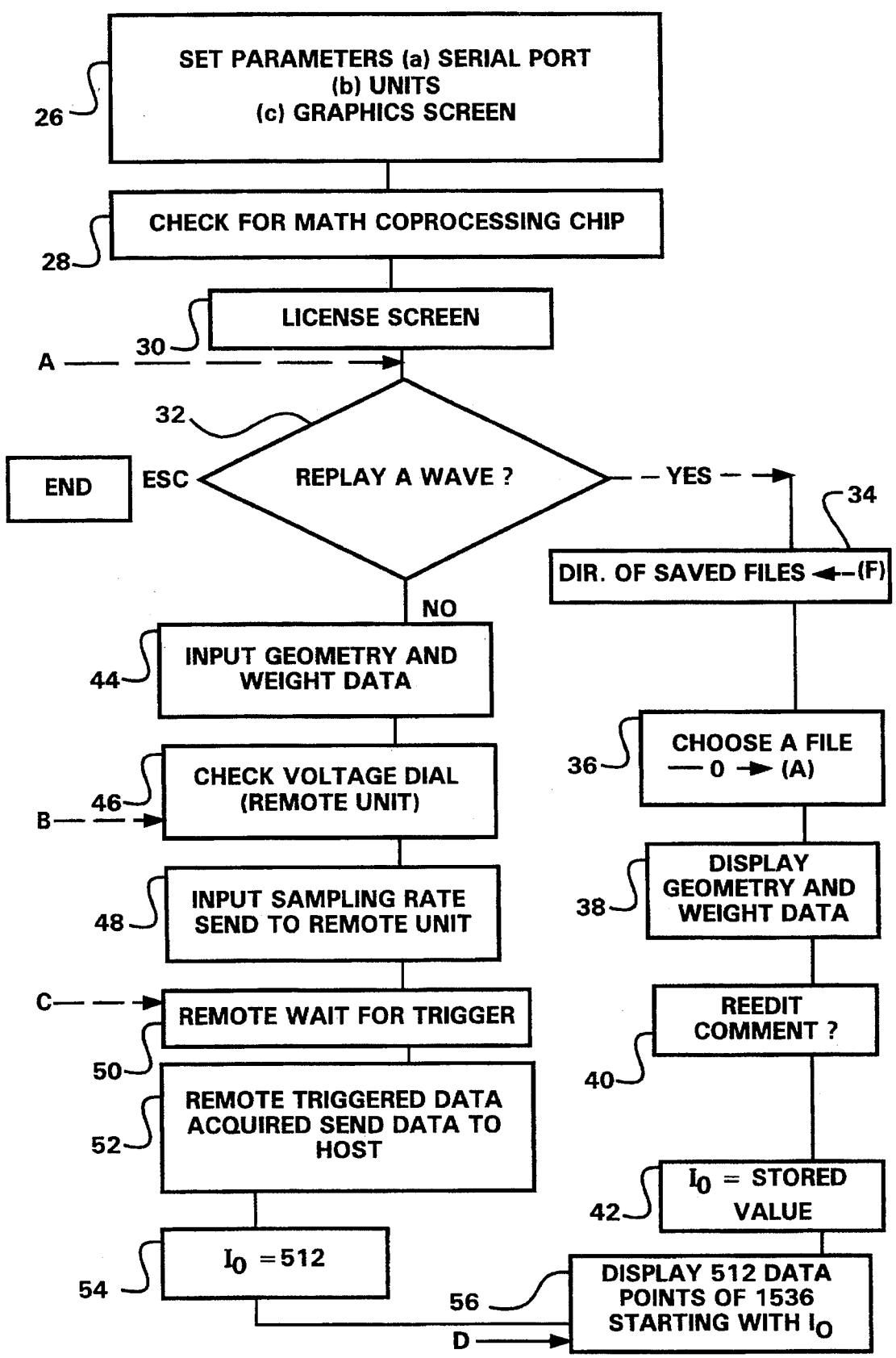
FIGS. 2A and 2B illustrate the flow chart for the method of the present invention.
Figure 2B:
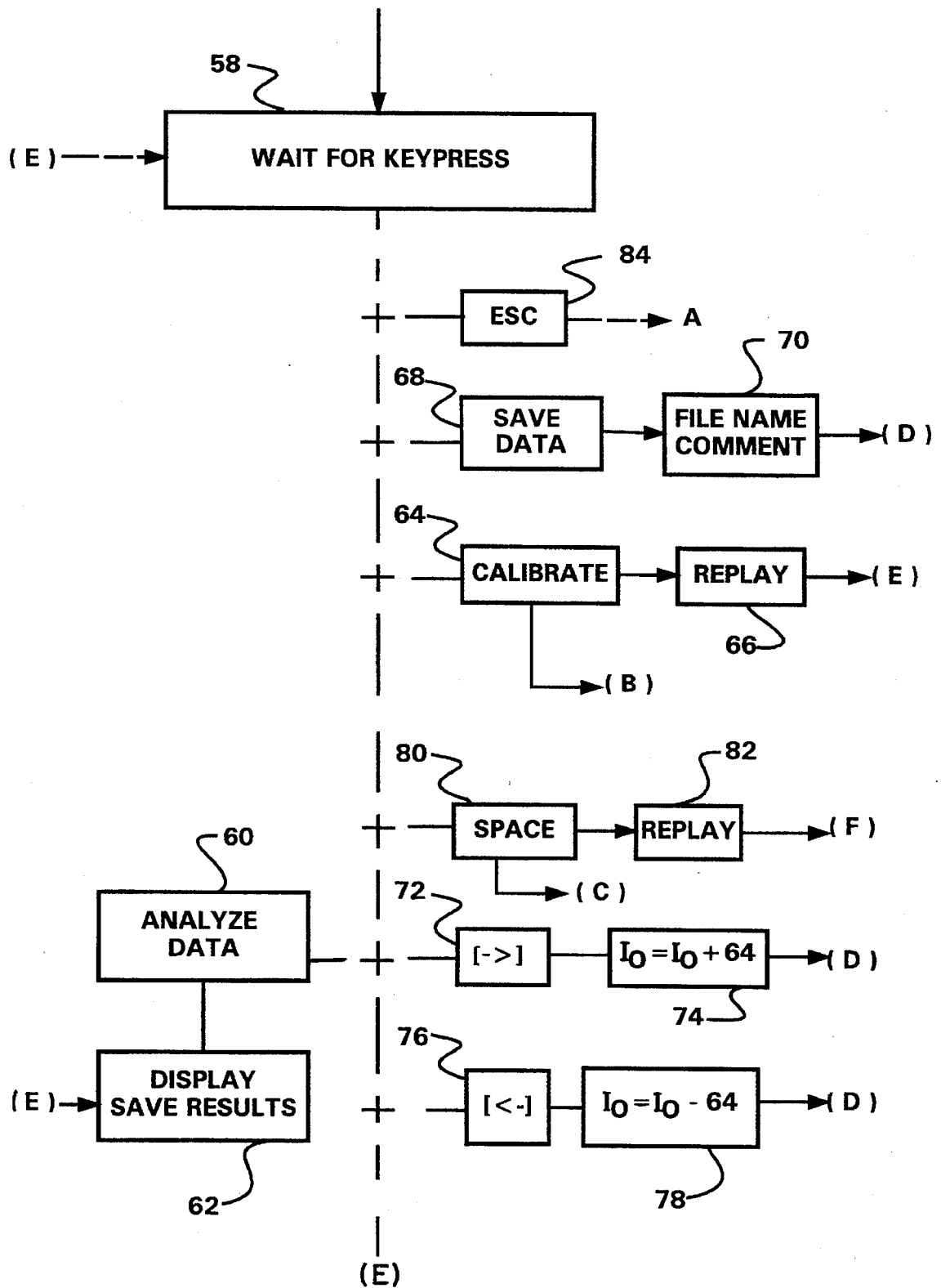

Referring now to FIGS. 2A and 2B, the implementation of the method is illustrated. The method is a software program which, in a broad sense, acquires, analyzes, calculates and saves data based on the vibrational patterns of the tube 24.

Initially, the user will be asked to "set parameters" as indicated by box 26. The system then internally checks for a math co-processor in box 28. If there is a math co-processor present, when the data is analyzed, Box 60, the program uses assembly language routines specifically written for the co-processor. If no co-processor is present, the data analysis can take up to 60 times as long to complete.

Box 30 is a license screen which is common throughout the computer industry.

In Box 32, the user is prompted and asked whether to replay a wave. If the user has tested a number of other tubes, there will be a directory listing of saved files. The user can then reanalyze one of the previous saved files related to the corresponding tube. Additionally, this feature allows the user to replay or reanalyze saved data without being connected to the computer hardware system 12. Accordingly, the system enters a directory of saved files in Box 34, and then the system displays the saved files for selection as set forth in Box 36. After the user chooses a file, the system displays the geometry and weight data of the particular chosen file in Box 38. Box 40 allows the user to edit any comments related to the particular file, and Box 42 presents the initial stored values.

If the user is starting a new test of a tube, the system requests the user to input the geometry and weight data in Box 44. The data relate to Equation [1] and are the parameters of the tube. These parameters are the core weight, length, span, outer core diameter, core wall thickness and an estimate of E.

Figure 3:
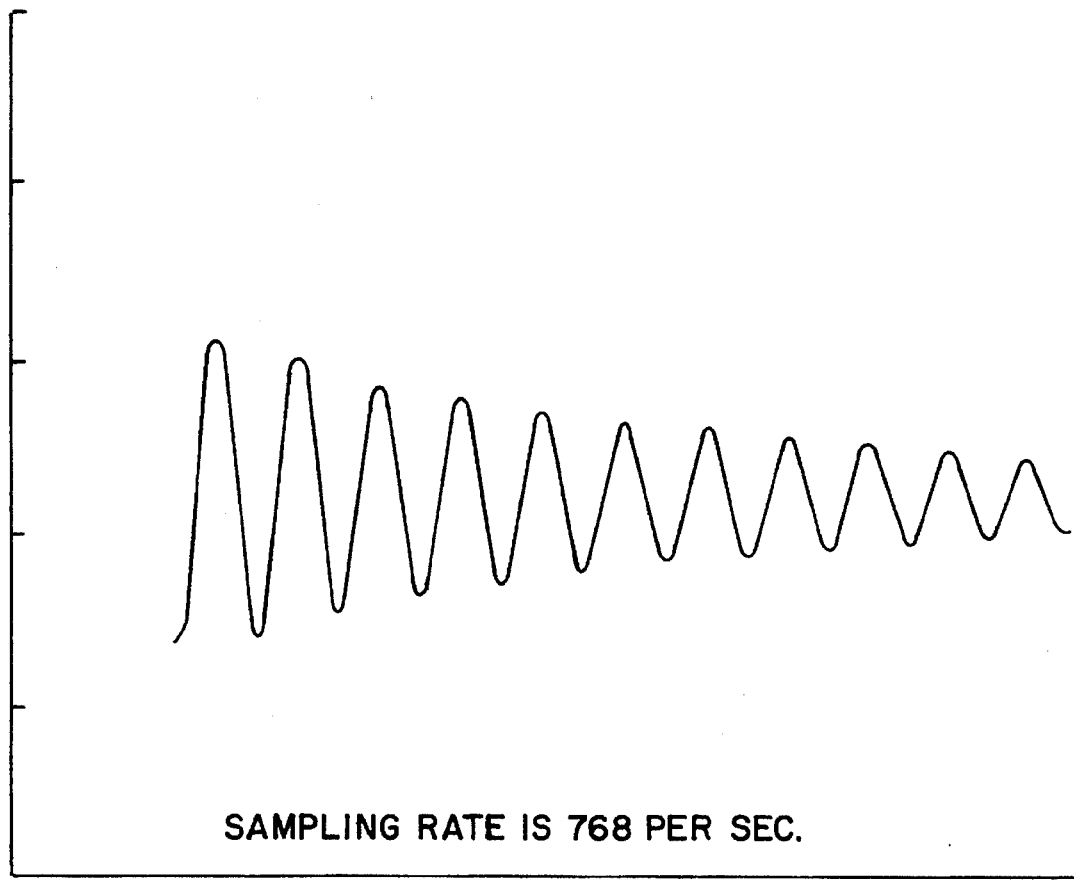
FIG. 3 is a sample computer screen output of a decaying sine wave generated by the present invention.

In Box 46, the system requires a check of the voltage amplifier dial and displays the old sampling rate while requesting a new sampling rate. If there is no change in the sampling rate, the system begins working with the old sampling rate. The estimate of E is to help determine a sampling rate. Ideally 8 to 12 cycles appear on the screen and are equivalent to 512 sample points. FIG. 3 illustrates a sampled wave displayed on this screen.

The voltage amplifier dial is a dial on the computer hardware system 12. The voltage regulation circuit 15 regulates the excitation voltage to the load cell 20 at a constant value. The Voltage Amplification Dial selects the amplification of the output voltage from the load cell 20. This signal conditioning circuit utilizes a Burr-Brown Instrument Amplifier INA110. The choice of amplification values are: 1, 10, 100, 110, 200, 210, 300, 310, 500, 510, 600, 610, 700, 710, 800, and 810.

For a 50 pound load cell, the readings would correspond to the following maxiums:

| Dial Reading | MaxLoad | |
|---|---|---|
| 0 | >50 lbs | the load cell maximum is 50 lbs |
| 1 | >50 lbs | the load cell maximum is 50 lbs |
| 2 | >50 lbs | the load cell maximum is 50 lbs |
| 3 | >50 lbs | the load cell maximum is 50 lbs |
| 4 | ~41.5 lbs | |
| 5 | ~39.6 lbs | |
| 6 | ~27.7 lbs | |
| 7 | ~26.8 lbs | |
| 8 | ~16.6 lbs | |
| 9 | ~16.3 lbs | |
| 10 | ~13.8 lbs | |
| 11 | ~13.6 lbs | |
| 12 | ~11.9 lbs | |
| 13 | ~11.7 lbs | |
| 14 | ~10.4 lbs | |
| 15 | ~10.2 lbs | |

If testing a 28 lb core, dial reading #6 is selected. This would show the wave mid-screen on the computer. With a 14 lb core, #10 is selected.

With the sampling rate as selected in Box 48, data are sent to the computer hardware system 12 and the system waits in Box 50 for the vibration of the tube to trigger the data acquisition section 14.

As soon as the tube begins to vibrate, the data acquisition section 14 is triggered and, as set forth in Box 52, the acquired data are sent to the host or compatible computer 22. Again, a wave similar to that shown in FIG. 3 is generated, and the data acquisition section 14 has collected 1536 data samples. Only 512 data samples are shown on the screen at one time initially, starting with $I_o$=512 (as shown in Box 54) which is the first sample. Box 56 indicates the display of the 512 data points of the 1536 data points starting with $I_o$.

As shown in FIG. 2B, the system now waits for the user to perform one of seven options.

1. If user wishes to analyze the wave (i.e., the 512 samples shown), the system moves to Box 60, analyzes the data and displays and saves the results in box 62. The system then goes back to Box 58 and awaits a further command.

2. The user can go to Box 64, calibrate the hardware dial reading, and enter a different sampling rate or, if replaying a wave, have the system move to Box 66, and then return to Box 58 for additional instructions.

3. The user can save the data by entering Box 68. The system then requests a file name and allows the user to attach any comments in Box 70. The system then moves to a display of the 512 data points as set forth in Box 56.

4. In Box 72, the user has the capability of increasing the starting position of the wave by 64 samples up to a point starting with the 1024th data point. After this option is entered, the system returns to Box 56 and displays 512 data points.

5. The user can also decrease the starting position of the wave by 64 samples down to a point starting with the 0th point. After the system calculates in Box 78, the program returns the user to Box 56 and a display of the chosen 512 data points.

6. The user or tester can again vibrate the tube 24 by entering Box 80, waiting for the vibration to trigger the data acquisition by returning to Box 50, or if replaying a wave, entering a directory of saved files from Box 34.

7. As a final option, the user can return to Box 32 through Box 84 and recommence the entire process.

After the system has analyzed the 512 data samples, the system will display a screen similar to FIG. 3, with the results set forth as nSEE (normalized standard error of estimate) which is the square root of the sum of (theory-experimental) squared divided by 512 divided by the average. In this way, any change in voltage amplification is taken into account. This number is only used on a relative basis. Accordingly, nSEE equals zero is a perfect match. The frequency is displayed and is calculated in hertz. D is the log decrement, and is calculated as set forth in equation E[4]. EI is core stiffness and E is the core modulus. Once again, at this point, the user will be given the same seven options as previously explained.

To obtain the high resolution of 0.001 Hz, a damped sine wave of the form $$y = B_1 e^{-(B_2 z)} \sin(2\pi B_3 z + B_4) + B_5$$

is fitted to the 512 Points using a nonlinear least squares (NLLS) techniques. Convergence to the correct parameters requires good initial estimates for the parameters. The following is the nonobvious process to obtain good initial estimates.

1) Average the 512 data. Set $B_5$=average.
2) Use a fast fourier transform on the 512 data. Set the peak frequency to $B_3$.
3) Divide 512 by $B_3$ to get number of cycles in 512 data. Determine amplitude of first and last cycles. Set amplitude of first cycle to $B_1$. Use the change in amplitude of the first and last cycles in determining estimate of $B_2$.
4) Utilize the first half cycle to determine the estimate of the phase shift $B_4$.

After the NLLS converges, the parameters of interest are:

$B_3$=frequency $B_5$=half weight of the specimen $B_2/B_3$=log decrement of the decaying sine wave.

While the above description contains many specificities, these should not be construed as limitations on the scope of the invention, but rather as exemplification of one preferred embodiment thereof. Many other variations are possible. Accordingly, the scope of the invention should be determined not by the embodiment illustrated, but by the appended claims and their legal equivalents.

I claim:

1. A system for nondestructive vibrational testing of an object, comprising:

load sensor means associated with the object and having an input for receiving a voltage input and an output for providing a sensor output, said load sensor means being responsive to said voltage input and to vibration of said object for generating said sensor output;

a hardware system connected to said load sensor means and responsive to said sensor output from said load sensor means for acquiring data relative to vibration of the object;

said hardware system including voltage regulating means connected to the input of said load sensor means for providing a regulated voltage input to said load sensor means;

said hardware system further including signal conditioning means connected to the output of said load sensor means for receiving and conditioning the sensor output from said load sensor means and capable to provide an amplified signal output, analog-to-digital converter means for receiving said amplified signal output from the signal conditioning means for converting said amplified signal output to a total of 1536 data samples in digital form; and a digital computer system responsive to said data samples, said digital computer system including means for selecting 512 data samples from the 1536 data samples, and analyzing the selected data samples.

2. The system of claim 1, wherein said computer system comprises means for determining rate of energy lost of the object.

3. The system of claim 1, wherein said means for selecting and analyzing determines at least one of core stiffness of the object and core modulus of the object.

4. The system of claim 1, wherein said computer system further comprises display means for displaying at least one of numerical results, graphical data and theoretical curves in response to said analyzed data samples, said display relating to the object.

5. The system of claim 4, wherein said computer system further includes means for calculating data corresponding to a normalized standard error and estimate for the object, said display means displaying the calculated data.

6. The system of claim 5, wherein said computer system further includes means for calculating data corresponding to at least one of frequency and log decrement of the object.

7. The system of claim 4, wherein said computer system further comprises means for storing generated data for saving original data and any additional data.

8. A system for nondestructive vibrational testing of an object, comprising:

load sensor means associated with the object and having an input for receiving a voltage input and an output for providing a sensor output, said load sensor means being responsive to said voltage input and to vibration of said object for generating said sensor output;

a hardware system connected to said load sensor means and responsive to said sensor output from said load sensor means for acquiring data relative to vibration of the object;

said hardware system including voltage regulating means connected to the input of said load sensor means for providing a regulated voltage input to said load sensor means;

said hardware system further including signal conditioning means connected to the output of said load sensor means for receiving and conditioning the sensor output from said load sensor means and capable to provide an amplified signal output, analog-to-digital converter means for receiving said amplified signal output from the signal conditioning means for converting said amplified signal output to a total of 1536 data samples in digital form; and a digital computer system responsive to said data samples said digital computer system including means for selecting 512 data samples from the 1536 data samples and for determining data corresponding to the rate of energy lost by the object.

9. The system of claim 8, wherein the object comprises one of paper core, tubes, wood beams or steel elements.

10. The system of claim 8, wherein said computer system further includes means for carrying out fast fourier transform operations upon the 512 selected data signals.

11. The system of claim 8, wherein said computer system further includes means for calculating a nonlinear least squares procedure from the 512 selected data signals.

12. The system of claim 11, wherein said means for calculating provides data indicative of or resolution to 0.001 Hz.

13. A system for nondestructive vibrational testing of an object, comprising:

load sensor means associated with the object and having an input for receiving a voltage input and an output for providing a sensor output, said load sensor means being responsive to said voltage input and to vibration of said object for generating said sensor output;

a hardware system connected to said load sensor means and responsive to said sensor output from said load sensor means for acquiring data relative to vibration of the object;

said hardware system including voltage regulating means connected to the input of said load sensor means for providing a regulated voltage input to said load sensor means;

said hardware system further including signal conditioning means connected to the output of said load sensor means for receiving and conditioning the sensor output from said load sensor means and capable to provide an amplified signal output, analog-to-digital converter means for receiving said amplified signal output from the signal conditioning means for converting said amplified signal output to a total of 1536 data samples in digital form; and a digital computer system including means for setting parameters for the object prompting the computer system for data by positioning an object inputting geometry and weight data of the specimen, checking a voltage dial setting of said signal conditioning means, inputting a sampling rate, setting initial sample data $I_o$ equal to the 512th sample point;

displaying 512 selected data samples of 1536 generated data samples starting with $I_o$;

waiting for a key press of input commands; and prompting the computer system again for data.

14. The system of claim 13 wherein prompting the system further comprises:

saving any previous data sampled;

providing a directory of saved files;

comparing a prompt of the system to the saved files and determining if a specimen has previously stored data;

displaying the geometry and weight data of the previously stored data;

reediting comments of the previously stored data;

setting $I_o$ equal to a stored value; and returning to the displaying of the geometry and weight data.

15. The system of claim 13, wherein waiting for the key press of input commands includes one of the following:

receiving a command generated by an input key and returning the computer system to the step of prompting;

receiving a command to save data, requesting a file name with comments, and returning the computer displaying;

receiving a command to calibrate the computer system, and returning to the checking;

receiving a command to resample a same specimen or list the data file for replay;

receiving a command to increase the starting position by 64 samples, and returning to the displaying of the geometry and weight data; and receiving a command to decrease the starting position by 64 samples, and returning to the displaying of the geometry and weight data.

16. The system of claim 13 wherein waiting for the key press of input commands further comprises:

receiving a command to analyze sampled data;

displaying the sampled data;

saving the results; and returning to the waiting for the key press of input commands.

17. A method for nondestructive vibrational testing, comprising the steps of:

setting parameters of a computer system;

checking for a math co-processor in the computer system;

prompting the computer system for data by positioning a specimen, inputting geometry and weight data of the specimen, checking a voltage dial setting, inputting a sampling rate, sending the data to a remote unit, waiting for an initial sample, and sending the initial sample to a host computer;

setting initial sample data $I_o$ equal to the 512th sample point;

displaying 512 data points of 1536 possible data points starting with $I_o$;

waiting for a key press of input commands; and prompting the computer system again for data.

18. The method for nondestructive vibrational testing according to claim 17, wherein the step of prompting the system further comprises the steps of:

saving any previous data sampled;

providing a directory of saved files;

comparing a prompt of the system to the saved files and determining if a specimen has previously stored data;

displaying the geometry and weight data of the previously stored data;

reediting comments of the previously stored data;

setting $I_o$ equal to a stored value; and returning to said step of displaying the geometry and weight data.

19. The method for nondestructive vibrational testing according to claim 17, wherein the step of waiting for the key press of input commands comprises one of the following steps:

receiving a command generated by an input key and returning the computer system to the step of prompting;

receiving a command to save data, requesting a file name with comments, and returning the computer system to the step of displaying;

receiving a command to calibrate the computer system, and returning to the step of checking;

receiving a command to resample a same specimen or list the data file for replay;

receiving a command to increase the starting position by samples, and returning to the step of displaying the geometry and weight data; and receiving a command to decrease the starting position by 64 samples, and returning to the step of displaying the geometry and weight data.

20. The method for nondestructive vibrational testing according to claim 17, wherein the step of waiting for the key press of input commands further comprises the steps of:

receiving a command to analyze sampled data;

displaying the sampled data;

saving the results; and returning to the step of waiting for the key press of input commands.

* * * * *